(12) United States Patent
Guo et al.

(10) Patent No.: US 12,082,803 B2
(45) Date of Patent: Sep. 10, 2024

(54) TISSUE SUTURING SYSTEM

(71) Applicant: JIANGSU TECH-BIO-MED MEDICAL EQUIPMENT CO., LTD., Jiangsu (CN)

(72) Inventors: Yanlin Guo, Jiangsu (CN); Wei Zhang, Jiangsu (CN)

(73) Assignee: JIANGSU TECH-BIO-MED MEDICAL EQUIPMENT CO., LTD., Jiangsu (CN)

( * ) Notice: Subject to any disclaimer, the term of this patent is extended or adjusted under 35 U.S.C. 154(b) by 0 days.

(21) Appl. No.: 18/140,443

(22) Filed: Apr. 27, 2023

(65) Prior Publication Data

US 2024/0008866 A1 Jan. 11, 2024

Related U.S. Application Data

(63) Continuation of application No. PCT/CN2023/076382, filed on Feb. 16, 2023.

(30) Foreign Application Priority Data

Jul. 5, 2022 (CN) .......................... 202210794207.5

(51) Int. Cl.
*A61B 17/04* (2006.01)
*A61B 17/06* (2006.01)

(52) U.S. Cl.
CPC .......... *A61B 17/0469* (2013.01); *A61B 17/06* (2013.01); *A61B 2017/06076* (2013.01)

(58) Field of Classification Search
CPC ................. A61B 17/0469; A61B 17/06; A61B 17/06076; A61B 17/049; A61B 17/06061
See application file for complete search history.

(56) References Cited

U.S. PATENT DOCUMENTS

| 5,499,991 | A | * | 3/1996 | Garman | ............. | A61B 17/0483 |
| | | | | | | 606/148 |
| 5,545,148 | A | * | 8/1996 | Wurster | ............. | A61B 17/0469 |
| | | | | | | 606/147 |
| 2007/0021755 | A1 | | 1/2007 | Almodovar | | |
| 2019/0388087 | A1 | | 12/2019 | Almodovar | | |
| 2021/0093320 | A1 | | 4/2021 | Smith | | |

FOREIGN PATENT DOCUMENTS

| CN | 113015491 A | 6/2021 |
| CN | 113456138 A | 10/2021 |
| CN | 115153698 A | 10/2022 |

* cited by examiner

*Primary Examiner* — Tuan V Nguyen
(74) *Attorney, Agent, or Firm* — SZDC Law PC

(57) ABSTRACT

A tissue suturing system includes: a first roller, a second roller, a first power unit, a second power unit and a suture needle. The suture needle is inserted and clamped between the first and second rollers, having parallel axes, at least one of the two rollers offering active rotation and the two rollers applying a force to the suture needle at the position where it is clamped. The first power unit is configured to provide a position where the first and second rollers are relatively close to each other so that their axes are parallel and the suture needle is clamped. The second power unit provides rotation power for the active rotation, and the suture needle is in form of a curved structure and driven by the active rotation to enter and exit the tissue following a curved direction, having an external exposed position for clamping by the two rollers.

4 Claims, 9 Drawing Sheets

TISSUE SUTURING SYSTEM

This application is a Continuation Application of PCT/CN2023/076382, filed on Feb. 16, 2023, which claims priority to Chinese Patent Application No. 202210794207.5, filed on Jul. 5, 2022, which is incorporated by reference for all purposes as if fully set forth herein.

TECHNICAL FIELD

The present invention relates to the technical field of tissue suturing, in particular to a tissue suturing system.

BACKGROUND

Laparoscopic suturing is one of the most difficult techniques to master in laparoscopic surgery. It is often very difficult for beginners because of the limitations of space and freedom of laparoscopic operation and the indirect operation using instruments.

The current routine laparoscopic suturing includes the following steps.

Needle and suture selection: Arc-shaped curved needles are generally used in the abdominal cavity, which is convenient for rotating needles under laparoscopy. The sutures must have certain elasticity to facilitate knotting.

Needle feeding: The suture is fed into the abdominal cavity through the operating hole at a set distance from the end of the needle with a needle holder or separating pliers.

Needle throwing: The suture needle is fed into the abdominal cavity and then naturally thrown in the field of view. The suture is thrown so that the needle is positioned at exactly the vertical angle formed after the needle holder clamps the needle as far as possible.

Needle adjustment and needle holding: When the needle is set, the left hand uses separating pliers to hold the suture and applies a pulling and rotating technique to adjust the needle so that it is placed in a position that exactly forms a vertical angle after the needle holder clamps the needle, that is, the needle holding position. Needle holding includes one-handed needle holding and two-handed needle holding, and needle adjustment includes one-handed needle adjustment and two-handed needle adjustment.

Suturing process: When entering the needle, the force acts on the tip of the needle and the force acts on the needle tip, and the force is applied along the direction of the needle exit and the curvature of the needle; when exiting the needle, the left hand holds the needle in the central front position with the pliers and the right hand fixes the tissued with the needle holder, the pliers in the left hand rotate the needle along the curvature of the needle and the right hand plucks the suture after the needle comes out, or the right hand operates the needle and the left hand plucks the suture.

The above-mentioned operation process is cumbersome to a certain extent. At present, a certain proportion of surgeons are still difficult to perform laparoscopic suturing operations even after training. An operating system that can reduce the difficulty of suturing and save suturing time is urgently needed in current surgery.

SUMMARY

The present invention provides a tissue suturing system to effectively solve the problems discussed above.

To this end, the present invention adopts technical solutions described below.

A tissue suturing system includes: a first roller, a second roller, a first power unit, a second power unit and a suture needle;

wherein the suture needle is inserted and clamped between the first and second rollers having parallel axes, at least one of the two rollers offering active rotation and the two rollers applying a force to the suture needle at the position where it is clamped;

wherein the first power unit is configured to provide a position where the first and second rollers are relatively close to each other so that their axes are parallel and the suture needle is clamped;

wherein the second power unit is configured to provide rotation power for the active rotation; and wherein the suture needle is in form of a curved structure and driven by the active rotation to enter and exit the tissue following a curved direction, and always having an external exposed position for clamping by the two rollers.

Further, the rotation power provided by the second power unit has a direction including both forward and reverse directions.

Further, the suture needle is an arc-shaped curved needle extending in a plane.

Further, the suture needle is a helical curved needle.

Further, the surface of the first and second rollers is correspondingly provided with a groove for accommodating the suture needle, the suture needle being simultaneously accommodated in the grooves of the two rollers.

Further, the first roller is provided with a groove for accommodating the suture needle, and the second roller is configured to squeeze a portion of the suture needle accommodated in the groove by a flat surface or a raised structure provided on the surface.

Further, the groove has a cross section including a straight line and/or a curved line.

Further, the first and second rollers move synchronously when they are moving close to each other.

Further, the first roller is relatively stationary and the second roller moves when they are moving close to each other.

Further, the relative movement between the first and second rollers is relative rotation and/or relative linear movement of the axis.

Further, when the relative movement between the first and second rollers is relative rotation, the first power unit includes a connecting rod, a power rod and an operating handle;

wherein one end of the connecting rod is fixedly connected with the roller set in motion, with its central part rotating around a preset rotation point, and the other end is provided with a sliding joint; and wherein one end of the power rod is connected to the sliding joint, and the other end is fixedly connected to the operating handle and driven by the operating handle to move in the axial direction to drive the connecting rod to rotate through the connecting joint during the movement.

Further, the second power unit is powered by a motor or a turning handle.

Further, the first roller and/or the second roller are of one piece, or of a layered structure including an outer layer and an inner layer.

Further, at least the outer layer of the first roller and/or the second roller is an elastic structure.

Further, when the relative movement between the first and second rollers is relative rotation, the first power unit includes: a mounting base, a connecting rod, a power rod and an operating handle;

wherein the mounting base is rotatably arranged around a first rotation shaft relative to a housing structure of the tissue suturing system;

wherein one end of the connecting rod is fixedly connected to the roller and the other end is connected to the mounting base, and at least one connecting rod is rotatably connected to the mounting base through a second rotation shaft, the second rotation shaft being perpendicular to the first rotation shaft and the connecting rod rotatably arranged being provided with a sliding connection position; and wherein the power rod is an elastic structure arranged inside the housing structure and having an extension direction in a natural state perpendicular to the first and second rotation shafts, one end of the power rod being slidably connected to the sliding connection position to provide power for the connecting rod rotatably arranged to rotate around the second rotation shaft and the other end being fixedly connected to the operating handle.

With the technical solutions of the present invention, the following technical effects can be achieved.

The present invention provides a suturing system that can effectively reduce the difficulty of tissue suturing, which changes the current methods of holding, adjusting, feeding and exiting suture needles. Specifically, with the two rollers that can hold the suture needle used as the power supply units for needle feeding and exiting, and with the needle holding action of the two rollers, the present invention makes it possible to drive the movement of two rollers through an external operation structure, thus synchronously driving the suture needle to carry out appropriate position change to realize the needle adjustment process. The above operation can effectively improve the efficiency of the suturing process, and the whole operation process can be accepted by more operators because of the reduced difficulty.

DESCRIPTION OF THE DRAWINGS

In order to more clearly illustrate the embodiments of the present invention or the technical solutions in the prior art, the accompanying drawings to be used in the description of the embodiments or prior art will be briefly described below. It is obvious that the accompanying drawings in the following description are only some of the embodiments recorded in the present invention, and other accompanying drawings can be obtained according to these accompanying drawings without creative work for those of ordinary skill in the art.

Figure 1:
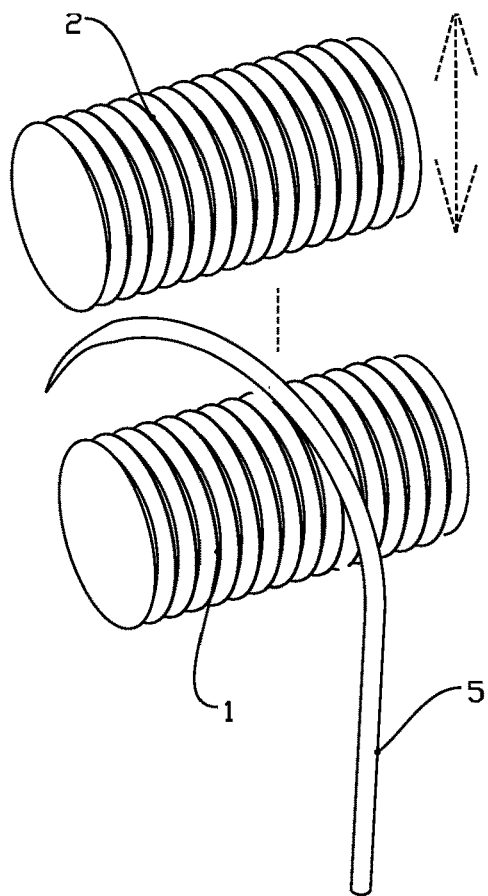
FIG. 1 is a schematic diagram of the relative linear movement of the two rollers when the suture needle is an arc-shaped curved needle.

Reference signs: 1. First roller; 11. Groove; 2. Second roller; 3. First power unit; 31. Connecting rod; 31a. Turning point; 31b. Waist-shaped hole; 32. Power rod; 32a. Bending area; 33. Operating handle; 34. mounting base; 4. Second power unit; 41. Motor; 42. Gear; 43. Turning handle; 5. Suture needle; 51. Needle tip; 52. Needle tail; 6. Tissue; 8. Housing structure.

DESCRIPTION OF THE EMBODIMENTS

The technical solutions in the embodiments of the present invention will be described clearly and completely in conjunction with the accompanying drawings in the embodiments of the present invention. Obviously, the described embodiments are only a portion of the embodiments of the present invention, rather than all the embodiments.

Unless otherwise defined, all technical and scientific terms used herein have the same meaning as commonly understood by those skilled in the art of the present invention. The terms used herein are for the purpose of describing specific embodiments only and are not intended to limit the invention. The term "and/or" as used herein includes any and all combinations of one or more of the related listed items.

As shown in FIGS. 1-8, the present invention provides a tissue suturing system, including: a first roller 1, a second roller 2, a first power unit 3, a second power unit 4 and a suture needle 5, wherein the suture needle 5 is inserted and clamped between the first and second rollers 1, 2 having parallel axes, at least one of the two rollers offering active rotation and the two rollers applying a force to the suture needle 5 at the position where it is clamped, wherein the first power unit 3 is configured to provide a position where the first and second rollers 1, 2 are relatively close to each other so that their axes are parallel and the suture needle is clamped, wherein the second power unit 4 is configured to provide rotation power for the active rotation, and wherein the suture needle 5 is in form of a curved structure and driven by the active rotation to enter and exit the tissue 6 following a curved direction, and always having an external exposed position for clamping by the two rollers.

The present invention provides a suturing system that can effectively reduce the difficulty of tissue suturing, which changes the current methods of holding, adjusting, feeding and exiting the suture needle 5. Specifically, with the two rollers that can hold the suture needle used as the power supply units for needle feeding and exiting, and with the needle holding action of the two rollers, the present invention makes it possible to drive the movement of two rollers through an external operation structure, thus synchronously driving the suture needle to carry out appropriate position change to realize the needle adjustment process. When the two rollers are fixed and not rotating, they can be used as jaws to hold the suture needle 5 for suturing. The above operation can effectively improve the efficiency of the suturing process, and the whole operation process can be accepted by more operators because of the reduced difficulty.

Figure 9:
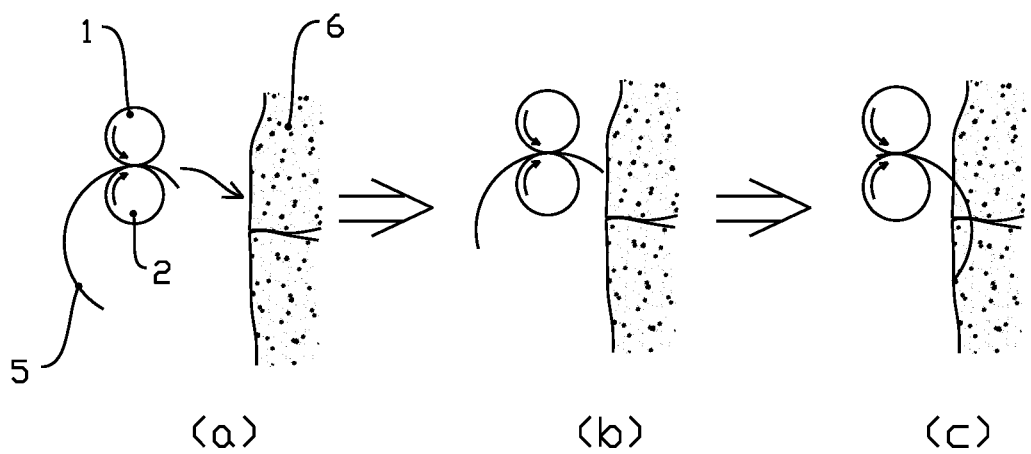
FIG. 9 is a schematic diagram of the needle feeding process of the arc-shaped curved needle.

FIG. 9 illustrates the process of feeding the suture needle 5. The needle 5 is clamped by the first and second rollers 1, 2 and brought to the specified position and direction by the clamping force, as shown in FIG. 9(*a*). The suture needle 5 is naturally thrown into the field of view after being sent into the abdominal cavity, so that the adjustment of the above position can be confirmed by a visualization equipment. During the needle feeding process, the needle tip 51 reaches the designated position, as shown in FIG. 9(*b*). The pair of two rollers provides the needle tip 51 with the force to penetrate the tissue 6. The second power unit 4 provides rotation power for the active rotation, so that the two rollers can rotate synchronously through the action of friction to drive the suture needle 5 to move along the curved direction to penetrate the suture position and lead out to another position of the tissue 6, as shown in FIG. 9(*c*).

Figure 10:
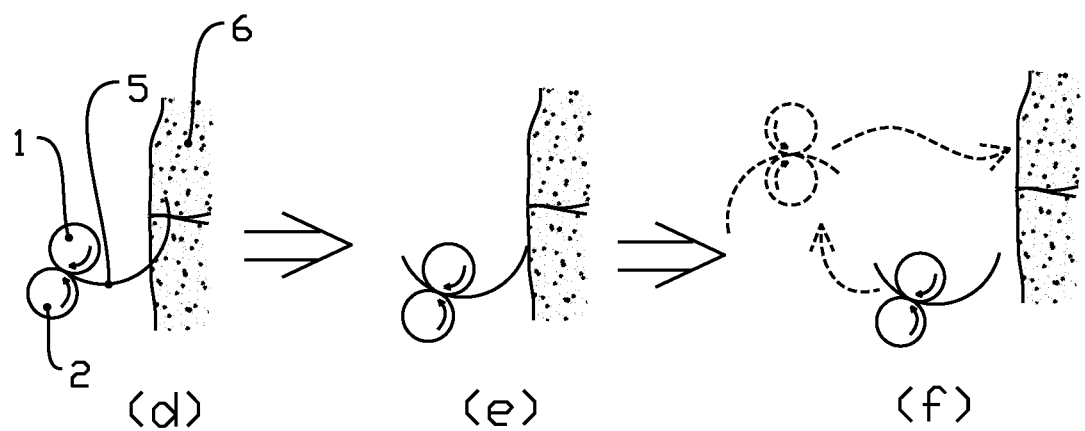
FIG. 10 is a schematic diagram of the needle exiting process of the arc-shaped curved needle.

FIG. 10 illustrates the process of exiting the suture needle 5. The needle tip 51 of the suture needle 5 is clamped by the first and second rollers 1, 2, as shown in FIG. 10(*d*). During the needle exiting process, the needle tail 52 is led out from the tissue 6 during the continuous rotation power output of the second power unit 4, as shown in FIG. 10(*e*). After the suture needle 5 is fully led out, it can participate in the next round of continuous suturing, as shown in FIG. 10(*f*).

Figure 11:
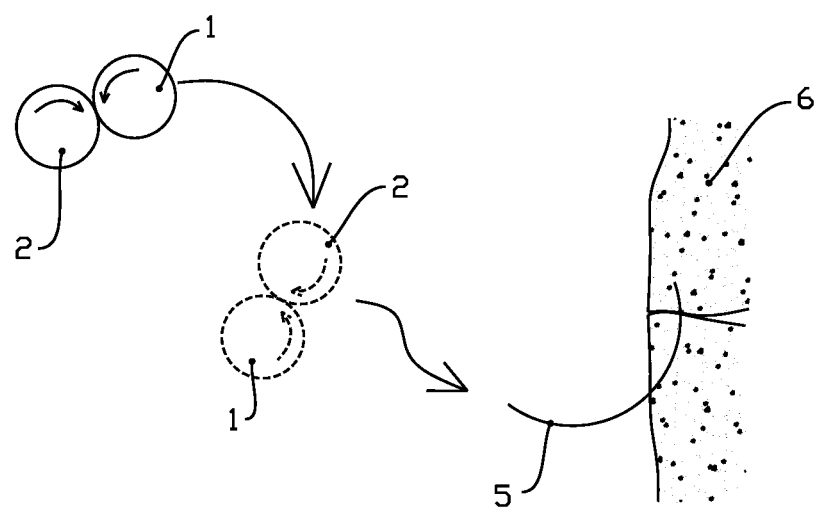
FIG. 11 is a schematic diagram of the two rollers rotating to provide power for the needle exiting.
Figure 12:
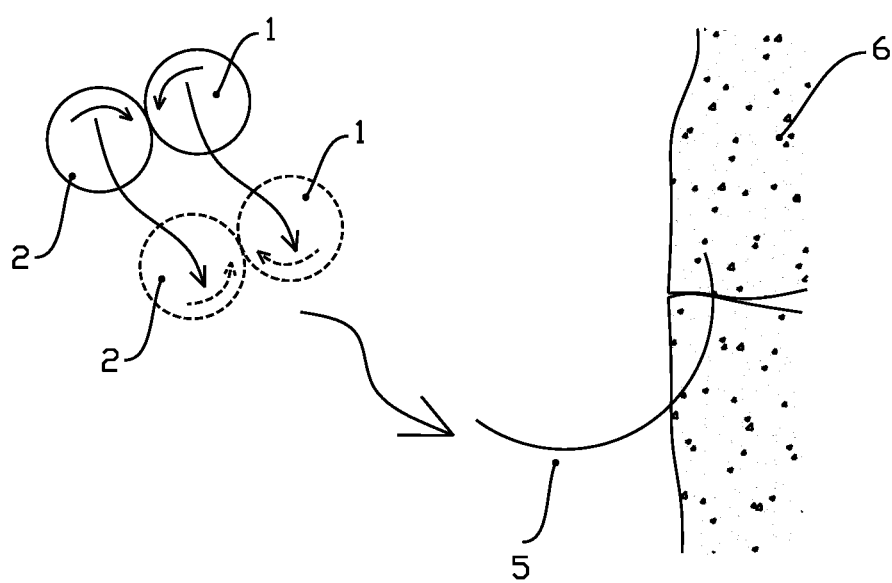
FIG. 12 is a schematic diagram of changing the rotation direction of the two rollers to provide power for the needle exiting.

In the above process, there must be a change in the direction of rotation of the needle 5 during the process of needle feeding and exiting. As shown in FIG. 10(*f*), the rotation direction of the two rollers in the upper dotted line is the needle feeding state, and the rotation direction of the two rollers in the lower solid line is the needle exiting state, the rotation direction of the upper and lower rollers are opposite. When the power direction is fixed, the above-mentioned direction change needs to be realized by the rotation of the two rollers at the operating end, as shown in FIG. 11. In this case, the change of the rotation direction is realized by changing the position of the rollers, or as another preferred way, the rotation power provided by the second power unit 4 has a direction including both forward and reverse directions. As shown in FIG. 12, the rotation direction of the rollers during needle feeding and exiting can be changed only through the change of power direction, which is obviously advantageous for reducing the difficulty of operation and minimizing the possible impact on the human body. The rollers shown in dotted line in FIGS. 11 and 12 represent the changed state.

Figure 2:
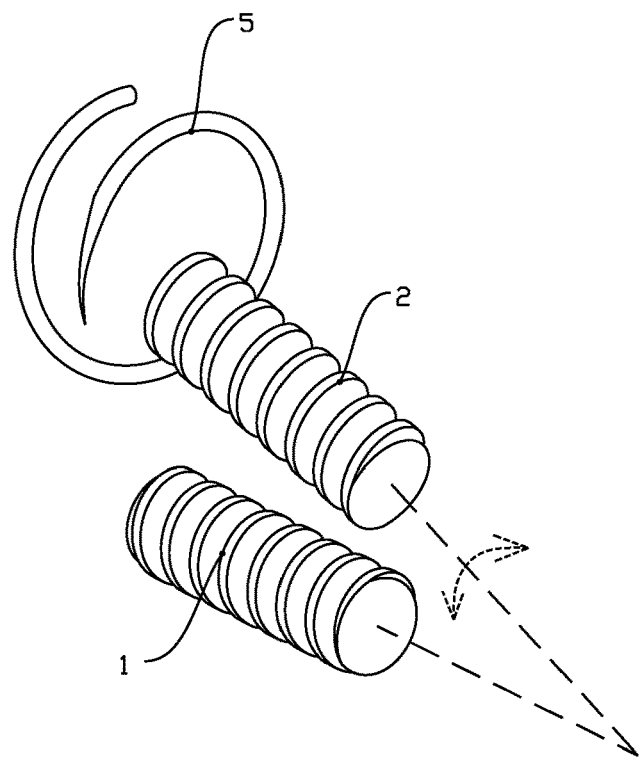
FIG. 2 is a schematic diagram of the relative rotation of the two rollers when the suture needle is a helical curved needle.
Figure 3:
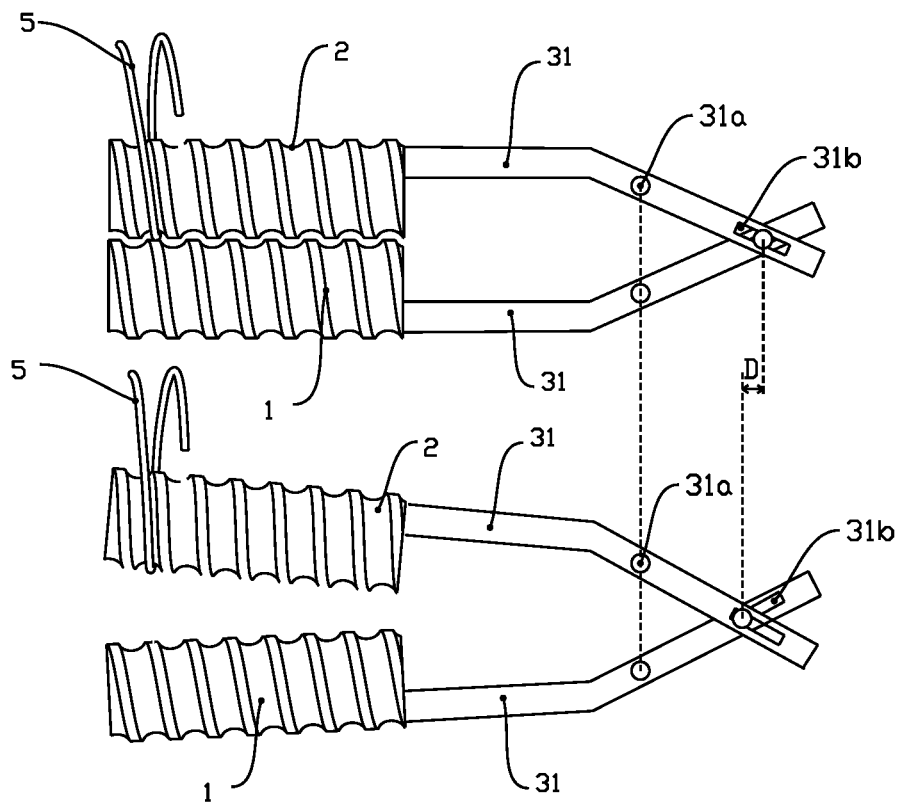
FIG. 3 is a schematic diagram of the process in which the two rollers are moving away from each other by rotation.
Figure 4:
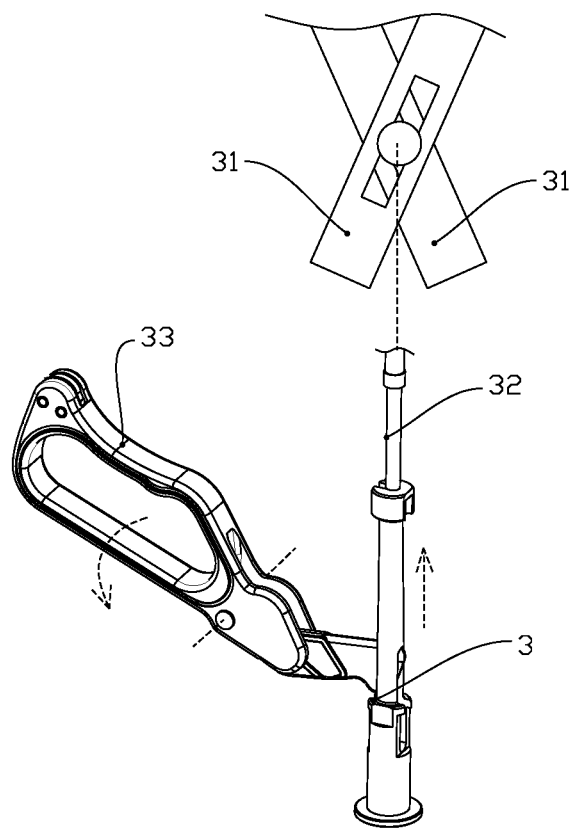
FIG. 4 is a schematic structural diagram of the first power unit.
Figure 8:
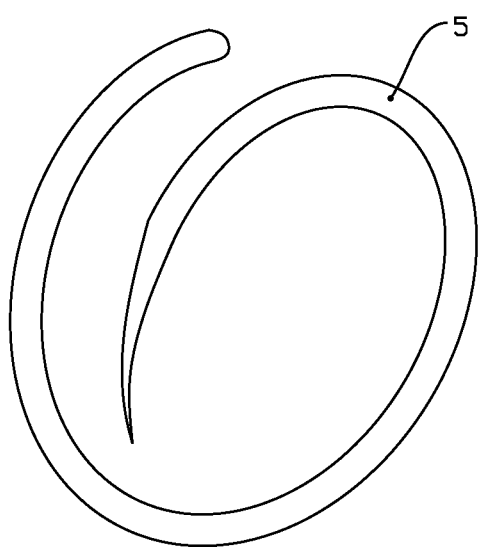
FIG. 8 is a schematic diagram when the suture needle is a helical curved needle.

For the suture needle, as long as it always has an external exposed position for the clamping by the two rollers, the suture needle 5 may be an arc-shaped curved needle extending in a plane, as shown in FIGS. 1 and 7, 9 to 12, respectively illustrating the configuration and working mode of such suture needle 5, or the suture needle 5 may be a helical curved needle as shown in FIGS. 2, 3 and 8, respectively illustrating the configuration and installation of the suture needle 5 relative to the rollers.

In the present invention, in order to enable the suture needle 5 to be clamped by the two rollers and enter and exit the tissue 6 following the bending direction during the active rotation of the rollers, the curvature of the suture needle 5 needs to be set sufficiently large. For example, when the suture needle 5 is an arc-shaped curved needle, it is necessary to ensure that the radius of the arc is large enough, so that after the roller enters the inner side of the needle, there is still a space between the needle and the roller to facilitate entry and exit of the tissue. When the suture needle 5 is helical, it is also necessary to ensure that the radius of the helical part is large enough, so as to achieve the same technical purpose aforementioned.

Figure 13:
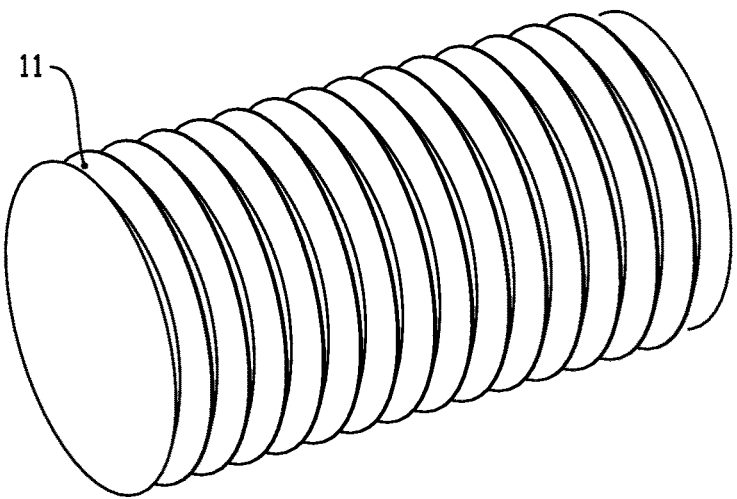
FIG. 13 is a schematic diagram of grooves provided on the surface of the roller.

As a preferred embodiment, the surface of the first and second rollers 1, 2 is correspondingly provided with a groove 11 for accommodating the suture needle 5, the suture needle 5 being simultaneously accommodated in the grooves 11 of the two rollers. In this case, the grooves 11 provided on the outside of the first and second rollers 1, 2 need to ensure the same parallel spacing, so that the suture needle 5 can always be accommodated simultaneously in the grooves 11 on both sides. It should be noted that the distribution of the grooves 11 needs to be adapted to the shape of the suture needle 5, specifically:

(1) When the suture needle 5 is an arc-shaped curved needle, because it is a structure extending in a plane, the groove 11 is set as a number of parallel grooves 11, as shown in FIG. 13, wherein two adjacent grooves 11 are independent of each other and the suture needle 5 cannot switch between the two grooves 11 during the suturing process, that is, the suture needle does not move along the axial direction of the roller.

(2) When the suture needle 5 is a helical curved needle, because it is a structure extending in three-dimensional space, the corresponding groove 11 needs to be set in a helical shape. During the suturing process of the helical needle, it will move along the helical trajectory and thus along the axial direction of the roller. In this case, it should be emphasized that the pitch of the helix of the suture needle 5 needs to be equal to the pitch of the helical grooves 11. In the above embodiment, the first and second rollers 1, 2 may adopt the same structure.

Alternatively, the first roller 1 is provided with a groove 11 for accommodating the suture needle 5, and the second roller 2 is configured to squeeze a portion of the suture needle accommodated in the groove 11 by a flat surface or a raised structure provided on the surface. In this case, the form of the groove 11 of the first roller 1 is consistent with the situation described in the above embodiment, while the second roller 2 has more structural possibilities:

(1) When the surface of the second roller 2 is a flat structure, it is necessary to ensure that the suture needle 5 is partially located outside the groove 11, thus ensuring that the second roller 2 is able to squeeze the suture needle 5, thus allowing the suture needle 5 to effectively obtain the frictional force that allows it to perform the suture action.

(2) When the surface of the second roller 2 is provided with a raised structure, the raised structure may be an intermediate raised portion formed by the provision of the groove 11, in which case the first roller 1 and the second roller 2 may be of the same structure, and the corresponding groove 11 and raised structure may be obtained by mere axial misalignment. Alternatively, the raised structure may be a more flexible circular or helical distribution area formed by juxtaposition of dotted protrusions to accommodate the suture needle 5, in which area the friction force is increased through the dotted raised structures.

Figure 14:
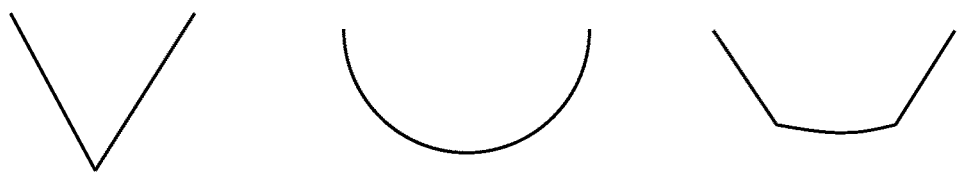
FIGS. 14(g)-(i) are schematic diagrams of three cross-sections of the grooves.

The groove 11 has a cross section including a straight line and/or a curved line, as shown in FIG. 14. In case (g), the cross section of the groove 11 is V-shaped and includes two straight lines; in case (h), the groove 11 is arc-shaped and includes a curved line; and in case (i), the cross section of the groove 11 is a special-shaped structure including two symmetrical straight lines and an intermediate curved line.

As a preferred embodiment, the first and second rollers 1, 2 move synchronously when they are moving close to each other. Alternatively, the first roller 1 is relatively stationary and the second roller 2 moves when they are moving close to each other.

Figure 5:
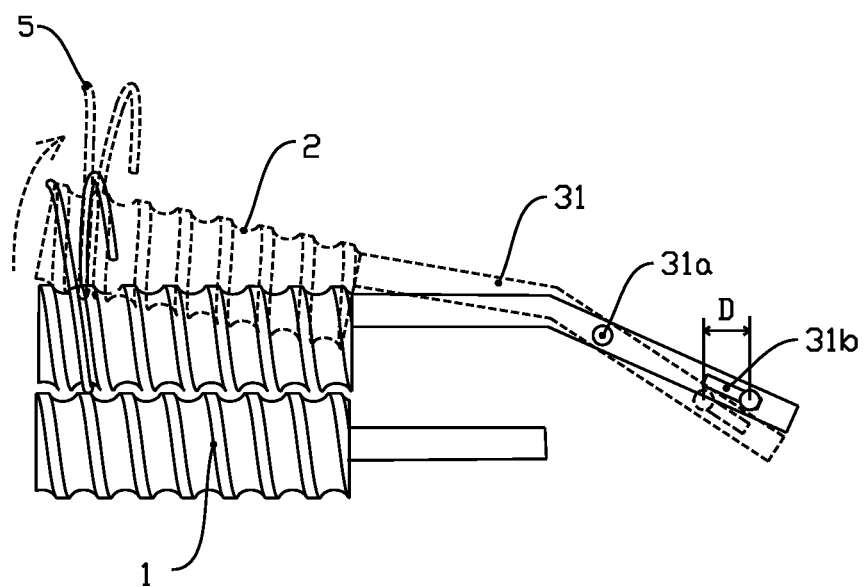
FIG. 5 is a schematic diagram of the process in which the first roller is stationary and the second roller is rotating.

The relative movement between the first and second rollers 1, 2 is relative rotation and/or relative linear movement of the axis. FIG. 1 illustrates the case where the relative movement is a linear movement and the linear direction is the radial direction of the rollers; FIG. 2 illustrates the case where the relative movement is rotation; FIG. 3 illustrates the case where the two rollers rotate synchronously; and FIG. 5 illustrates the case where the first roller 1 is relatively stationary and the second roller 2 rotates relative to the first roller 1.

When the relative movement between the first and second rollers 1, 2 is relative rotation, as a specific implementation, the first power unit 3 includes a connecting rod 31, a power rod 32 and an operating handle 33, wherein one end of the connecting rod 31 is fixedly connected with the roller set in motion, with its central part rotating around a preset rotation point 31a, and the other end is provided with a sliding joint, and wherein one end of the power rod 32 is connected to the sliding joint, and the other end is fixedly connected to the operating handle 33 and driven by the operating handle 33 to move in the axial direction to drive the connecting rod 31 to rotate through the connecting joint during the movement.

Specifically, the sliding joint may be provided as a waist-shaped hole 31b. One end of the power rod 32 is connected to the pin of the waist-shaped hole 31b, and the other end is fixedly connected to the operation handle 33 and driven by the operating handle 33 to move in the axial direction to drive the pin to slide within the waist-shaped hole 31b.

As shown in FIG. 3, the power rod 32 drives the pin to move a distance D. In the process of sliding the pin along the waist-shaped hole 31b, the connecting rod 31 is limited by the rotation point 31a, so it will inevitably be driven by the power rod 32 to rotate, thus realizing the synchronous relative rotation of the first and second rollers 1, 2. FIG. 5 demonstrates the rotation of the second roller 2, the working principle of which is described above and here will not be repeated.

Figure 6:
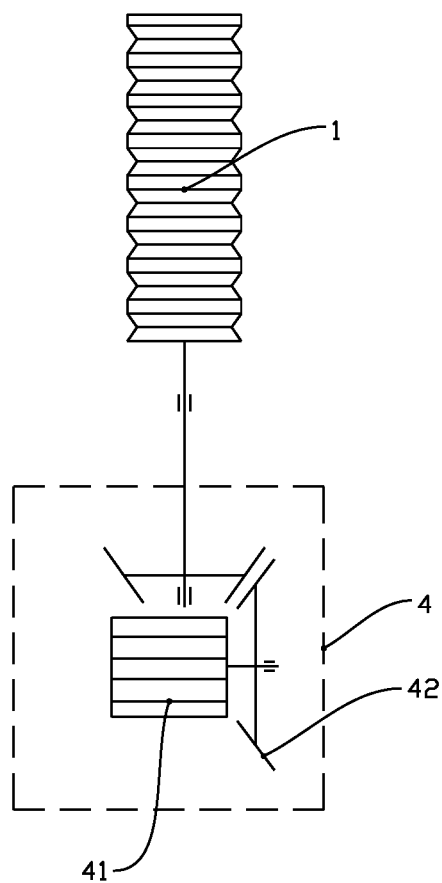
FIG. 6 is a schematic structural view of the second power unit.
Figure 7:
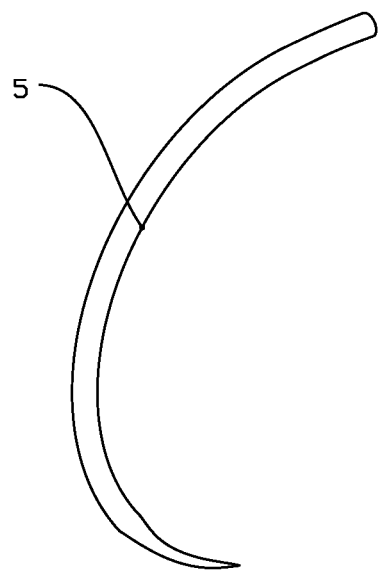
FIG. 7 is a schematic diagram when the suture needle is an arc-shaped curved needle.
Figure 15:
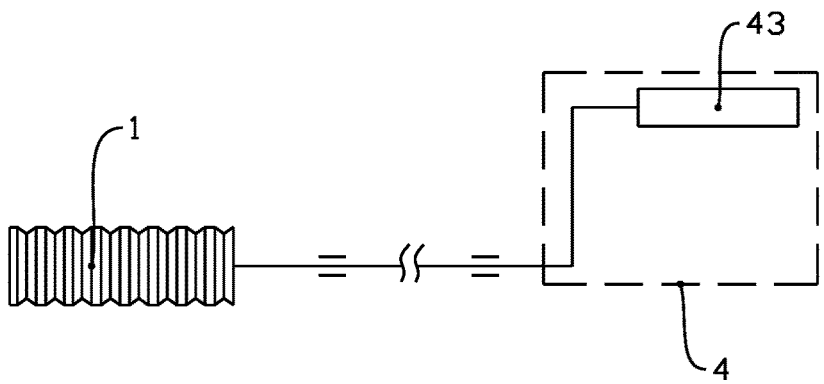
FIG. 15 is another schematic structural view of the second power unit.

The second power unit 4 is powered by a motor 41 or a turning handle 43. As shown in FIG. 6, the second power unit 4 is powered by a motor 41, which can be selected from the existing micro-motors. In order to adapt to the axial direction of the power shaft of motor 41, a matching transmission structure may be provided, or the power shaft of motor 41 may be directly connected to the rotation shaft of the roller. FIG. 6 illustrates a transmission structure including two gears 42, where the type and orientation of the gear 42 may be selected based on the axial direction of the power shaft of the specific motor 41 and the rotation shaft of the roller. As shown in FIG. 15, the second power unit 4 is powered by a turning handle 43. Unlike the above case where the motor 41 needs to be placed inside or outside the housing structure of the suturing system, the turning handle 43 must be located outside the housing structure for operation and always kept out of the human body.

Figure 16:
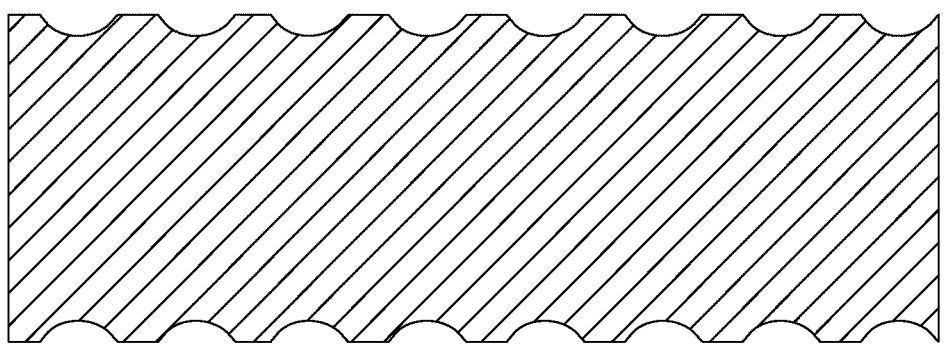
FIG. 16 is a cross-sectional view of the roller having a one-piece structure.
Figure 17:
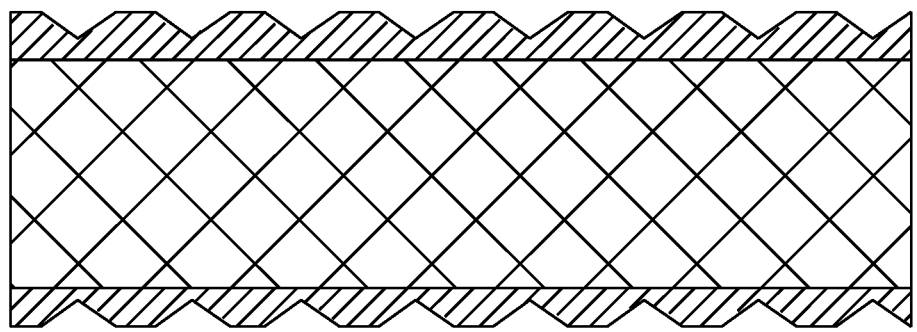
FIG. 17 is a cross-sectional view of the roller having a layered structure including an outer layer and an inner layer.

As a preferred embodiment, the first roller 1 and/or the second roller 2 are of one piece, or of a layered structure including an outer layer and an inner layer. FIGS. 16 and 17 illustrate the cross section of a one-piece roller structure and a layered roller structure, respectively. As a preferred embodiment, at least the outer layer of the first roller 1 and/or the second roller 2 is an elastic structure. As shown in FIG. 16, when the roller is of a one-piece structure, it can be a rigid structure as a whole. Since the roller works inside the human body, in order to better adapt to the actual space, orientation and tissue 6, as a preferred embodiment, the roller is an elastic structure as a whole. Alternatively, as shown in FIG. 17, the roller may be a layered structure having an elastic outer layer. This allows the roller structure to be more adapted to the suture needle 5 which is affected by the reaction forces of the tissue 6 during the suturing process, adapting to the deformation of the tissue 6 on the one hand and the deformation of the suture needle 5 on the other.

Figure 18:
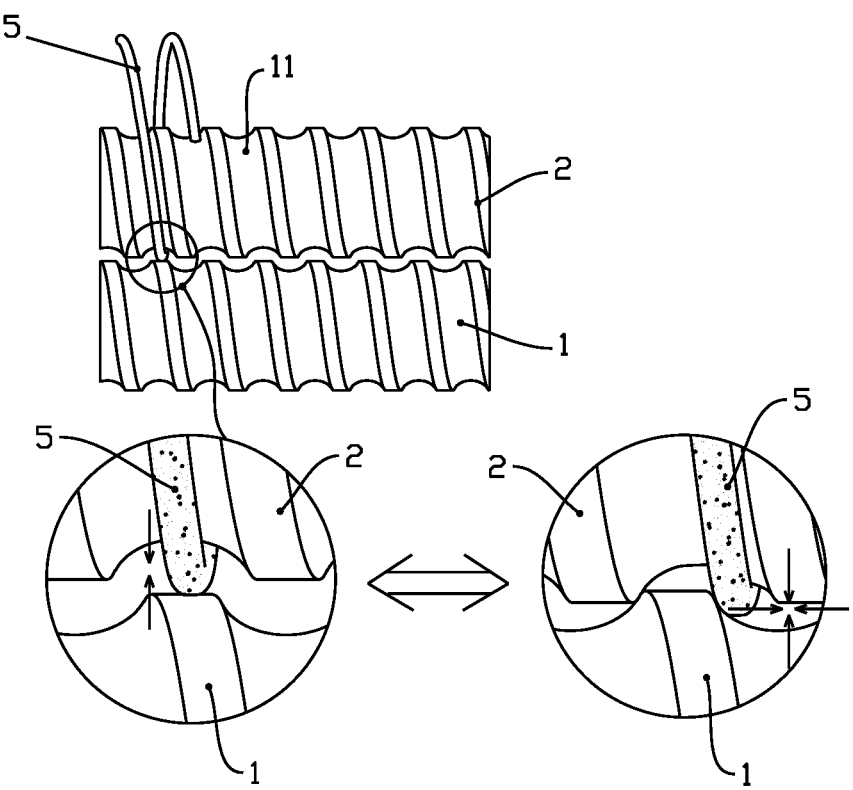
FIG. 18 is a comparison diagram of the squeezing of the suture needle before and after deformation of the rollers due to the elasticity of the outer layer.

Of course, the inner layer of the layered structure may be rigid or also be elastic, but more rigid than the outer layer. The above-mentioned elastic structure is even more advantageous when the suture needle 5 is helical. The forces on the helical suture needle 5 are relatively complex, and the elastic structure can better cope with the actual forces on the suture needle 5 and better transmit friction to the suture needle 5 through its own deformation. As shown in FIG. 18, the deformation of the elastic structure allows the application of forces to the needle 5 in more directions, such as in the up and down directions shown on the left side of the figure, and in multiple directions as shown on the right side of the figure.

Figure 19:
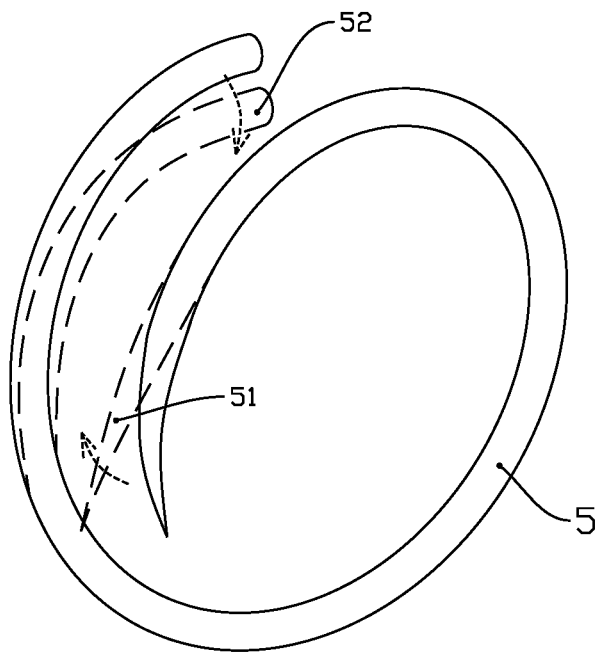
FIG. 19 is an optimized schematic diagram of a helical suture needle.
Figure 20:
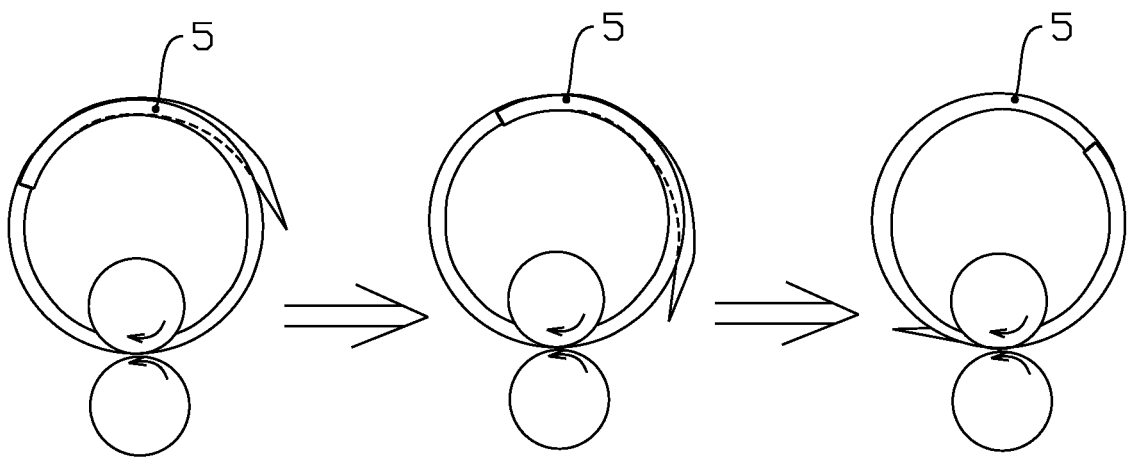
FIG. 20 is a schematic diagram of the process of suturing with the optimized suture needle in FIG. 19.

In order to achieve a better suture effect, when the suture needle 5 is helical, as shown in FIG. 19, the needle tip 51 of the suture needle 5 preferably spreads outwards. In this way, as shown in FIG. 20, during the needle feeding process, the needle tip 51 is closer to the tissue 6 than the needle tail 52 to better penetrate the tissue 6, avoiding insufficient needle penetration depth caused by the compression of the needle tail 52 on the tissue 6. Of course, the needle tail 52 of the suture needle 5 may preferably fold inwards to achieve the same technical effects.

In order to be more adaptable to complex suturing positions, when the relative movement between the first and second rollers is relative rotation, the first power unit 3 includes: a mounting base 34, a connecting rod 31, a power rod 32 and an operating handle 33, wherein the mounting base 34 is rotatably arranged around a first rotation shaft relative to a housing structure 7 of the tissue suturing system, wherein one end of the connecting rod 31 is fixedly connected to the roller and the other end is connected to the mounting base 34, and at least one connecting rod 31 is rotatably connected to the mounting base 34 through a second rotation shaft, the second rotation shaft being perpendicular to the first rotation shaft and the connecting rod 31 rotatably arranged being provided with a sliding connection position; and wherein the power rod 32 is an elastic structure arranged inside the housing structure 8 and having an extension direction in a natural state perpendicular to the first and second rotation shafts, one end of the power rod 32 being slidably connected to the sliding connection position to provide power for the connecting rod 31 rotatably arranged to rotate around the second rotation shaft and the other end being fixedly connected to the operating handle 33.

Figure 21:
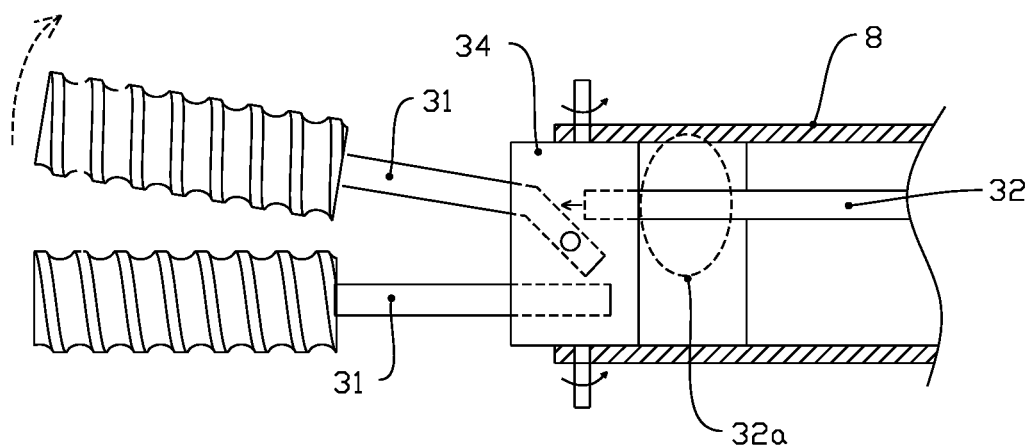
FIG. 21 is another schematic structural diagram of the first power unit.
Figure 22:
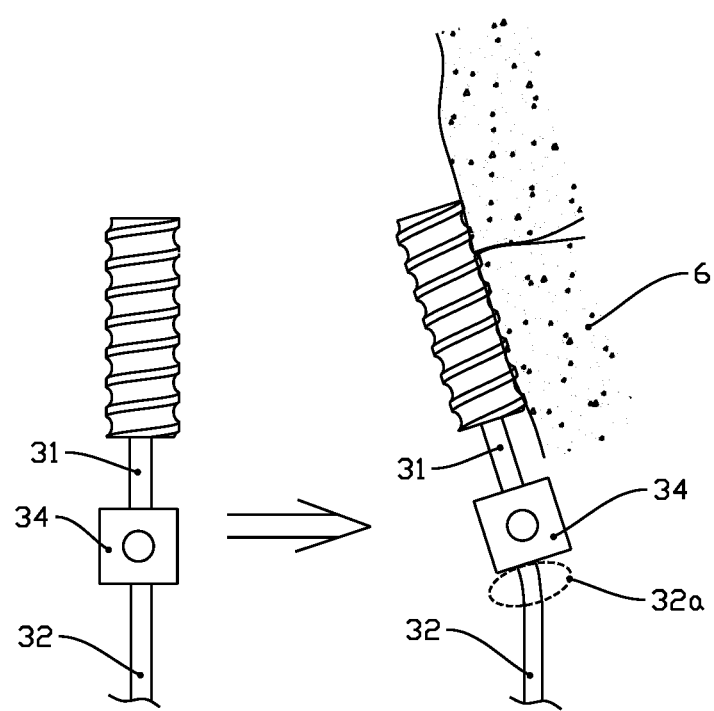
FIG. 22 is a schematic diagram of the deformation process of the power rod of the first power unit in FIG. 21.

FIG. 21 illustrates an embodiment in which the connecting rod 31 connected to one roller is fixedly connected to the mounting base 34 and the connecting rod 31 connected to the other roller is rotatably connected to the mounting base 34. When the position of the tissue 6 to be sutured requires the change of the angle of the axis of the rollers with respect to the direction of extension of the power rod 32, the two rollers can be placed against the tissue 6 as shown in FIG. 22, and the rollers are adapted to the direction of the tissue 6 by the blockage of the tissue 6 and by the continuous application of force through the operating handle 33. At this time, the mounting base 34 is rotated about the first rotation shaft with respect to the housing structure 8, and since the end of the power rod 32 is slidingly connected to the sliding connection position of the connecting rod 31, the end of the power rod 32 will be rotated synchronously during the rotation of the mounting base 34, thereby causing the power rod 32 to bend, thus forming a bending area 32a. It should be noted that when the rotation shaft of the second power unit 4 passes through this area, a connecting shaft structure is required to realize transmission of the rotating power under the angle change.

The basic principles, main features and advantages of the present invention have been shown and described above. Those skilled in the industry should understand that the present invention is not limited by the foregoing embodiments. The foregoing embodiments and descriptions only illustrate the principles of the present invention. Without departing from the spirit and scope of the present invention, the present invention will have various changes and improvements, which fall within the scope of the claimed invention. The scope of protection claimed by the present invention is defined by the appended claims and their equivalents.

The invention claimed is:

1. A tissue suturing system comprising: a first roller, a second roller, a first power unit, a second power unit and a suture needle;
   wherein the suture needle is inserted and clamped between the first and second rollers having parallel axes, at least one of the two rollers offering active rotation and the two rollers applying a force to the suture needle at the position where it is clamped;
   wherein the first power unit is configured to provide a position where the first and second rollers are relatively close to each other so that their axes are parallel and the suture needle is clamped;
   wherein the second power unit is configured to provide rotation power for the active rotation;
   wherein the suture needle is in form of a curved structure and driven by the active rotation to enter and exit the tissue following a curved direction, and always having an external exposed position for clamping by the two rollers;
   wherein the first roller is provided with a groove for accommodating the suture needle, and the second roller is configured to squeeze a portion of the suture needle accommodated in the groove by a flat surface or a raised structure provided on the surface; wherein the suture needle is a helical curved needle; wherein a needle tip of the suture needle spreads outward, a needle tail is inwards into a state of closure, wherein the corresponding groove is arranged in a spiral shape; wherein at least the outer layer of the first roller and/or the second roller is an elastic structure;
   wherein in a process of feeding the suture needle, the needle is clamped by the first and second rollers, and brought to a predetermined position and direction by an clamping force of the first and second rollers, the suture needle is returned to a field of view after being sent into an abdominal cavity, so that an adjustment of the predetermined position can be confirmed by a visualization equipment; during the needle feeding process, the needle tip reaches the designated position, the pair of two rollers provides the needle tip with the force to penetrate the tissue, the second power unit provides rotation power for the active rotation, so that the two rollers can rotate synchronously through the action of friction to drive the suture needle to move along the curved direction to penetrate the suture position and lead out to another position of the tissue;
   wherein the rotation power provided by the second power unit has a direction including both forward and reverse directions; the rotation direction of the rollers during needle feeding and exiting can be changed through the change of power direction;
   wherein the first and second rollers move synchronously when they are moving close to each other;
   wherein a relative movement between the first and second rollers is relative rotation and/or relative linear movement of the axis;
   wherein when the relative movement between the first and second rollers is relative rotation, the first power unit comprises: a mounting base, a connecting rod, a power rod and an operating handle;
   wherein the mounting base is rotatably arranged around a first rotation shaft relative to a housing structure of the tissue suturing system;
   wherein one end of the connecting rod is fixedly connected to the roller and the other end is connected to the mounting base, and the connecting rod is rotatably connected to the mounting base through a second rotation shaft, the second rotation shaft being perpendicular to the first rotation shaft, and the connecting rod rotatably arranged being provided with a sliding connection position; and
   wherein the power rod is an elastic structure arranged inside the housing structure and having an extension direction in a natural state perpendicular to the first and second rotation shafts, one end of the power rod being slidably connected to the sliding connection position to provide power for the connecting rod rotatably arranged to rotate around the second rotation shaft and the other end being fixedly connected to the operating handle.

2. The tissue suturing system according to claim 1, wherein the suture needle has a cross section comprising a straight line and/or a curved line.

3. The tissue suturing system according to claim 1, wherein the first roller is relatively stationary and the second roller moves when they are moving close to each other.

4. The tissue suturing system according to claim 1, wherein the second power unit is powered by a motor or a turning handle.

\* \* \* \* \*